United States Patent [19]

Barr

[11] Patent Number: Plant 5,656

[45] Date of Patent: Feb. 4, 1986

[54] DWARF NANDINA—GULF STREAM

[75] Inventor: William C. Barr, Rosenberg, Tex.

[73] Assignee: Weyerhaeuser Company, Tacoma, Wash.

[21] Appl. No.: 553,711

[22] Filed: Nov. 21, 1983

[51] Int. Cl.[4] ..... A01H 5/00

[52] U.S. Cl. ..... Plt./54

[58] Field of Search ..... Plt./54

[56] References Cited

PUBLICATIONS

Wholesale Catalog for 1962–1963, Monrovia NSY Co., Azusa, CA, pp. 62 and 64.

*Primary Examiner*—Robert E. Bagwill

[57] ABSTRACT

A dwarf nandina having densely foliaged and ascending branches, resulting in a rounded, compact shape.

3 Drawing Figures

BACKGROUND OF THE INVENTION

The present invention relates to a new and distinct plant variety of *Nandina domestica* (Thunberg), commonly known as Heavenly Bamboo, in the Berberidaceae family.

SUMMARY OF THE INVENTION

This new variety was discovered at Hines Wholesale Nurseries, P.O. Box 42284, Houston, Tex. 77242. The new variety originated as a mutant in the cultivar, *Nandina domestica* 'Compacta,'. The distinctive plant was identified in a population of asexually produced plants of similar age and culture. The plant was selected and isolated as a distinctive form for further evaluation. The new variety has been reproduced numerous times by asexual propagation (vegetative cuttings). Several hundred plants exist. Each of the progeny exhibit identical characteristics to the original mutant plant, establishing the variety as stable and true to type.

This new variety has many desirable, distinctive characteristics which render it unique from the original parent cultivar and the common species. The overall appearance of the new variety is a dwarf, symmetrical, densely compact, solitary form. The plant branches freely from basal and lateral buds. The foliage is held slightly erect and occurs in a high density fashion. The individual leaf is 2–3 pinnately compound. The individual leaflet is ovate to lanceolate and slightly concave. The leaves upon emergence are multicolored, in hues of green, orange, copper, and reddish bronze; maturing into a medium green color. Fall coloration ranges from orange through red, being more intense in cold temperatures.

The accompanying color photographs serve to illustrate the new plant variety, wherein:

DETAILED PLANT DESCRIPTION

Figure 1:
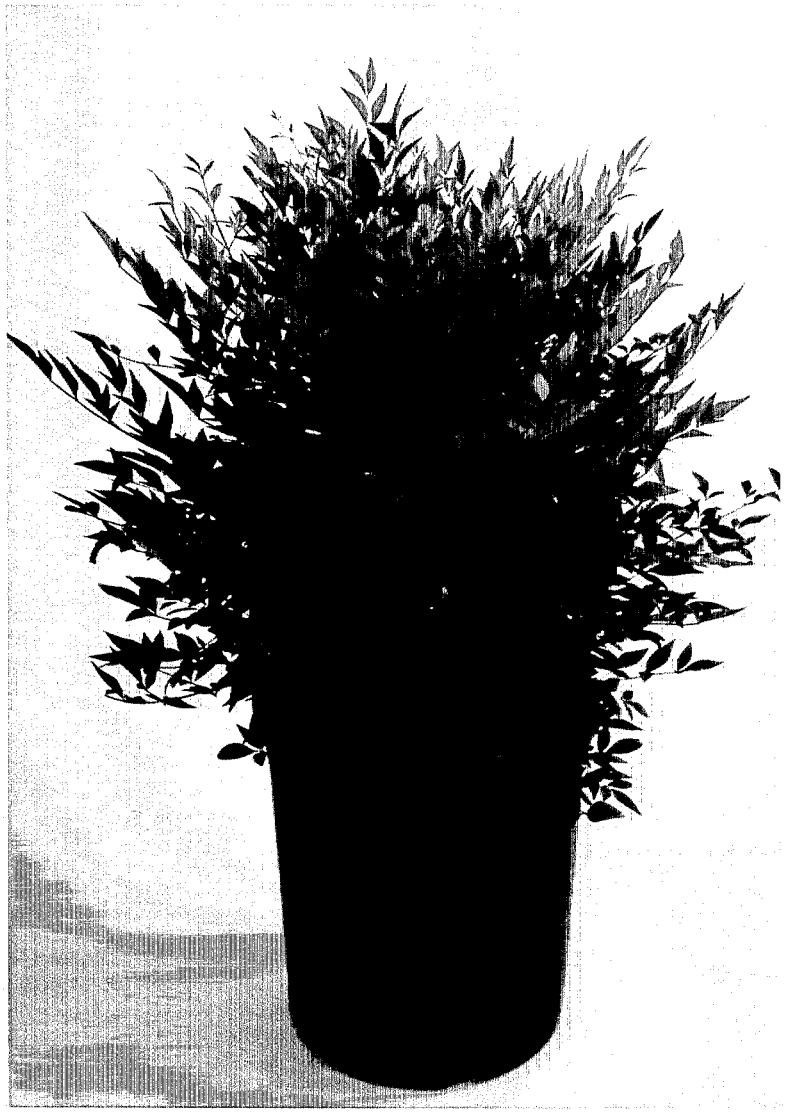
FIG. 1 is a color photograph of an unpruned individual plant of the new variety, growing in a 5-gallon container at an age of 22 months from cutting.
Figure 2:
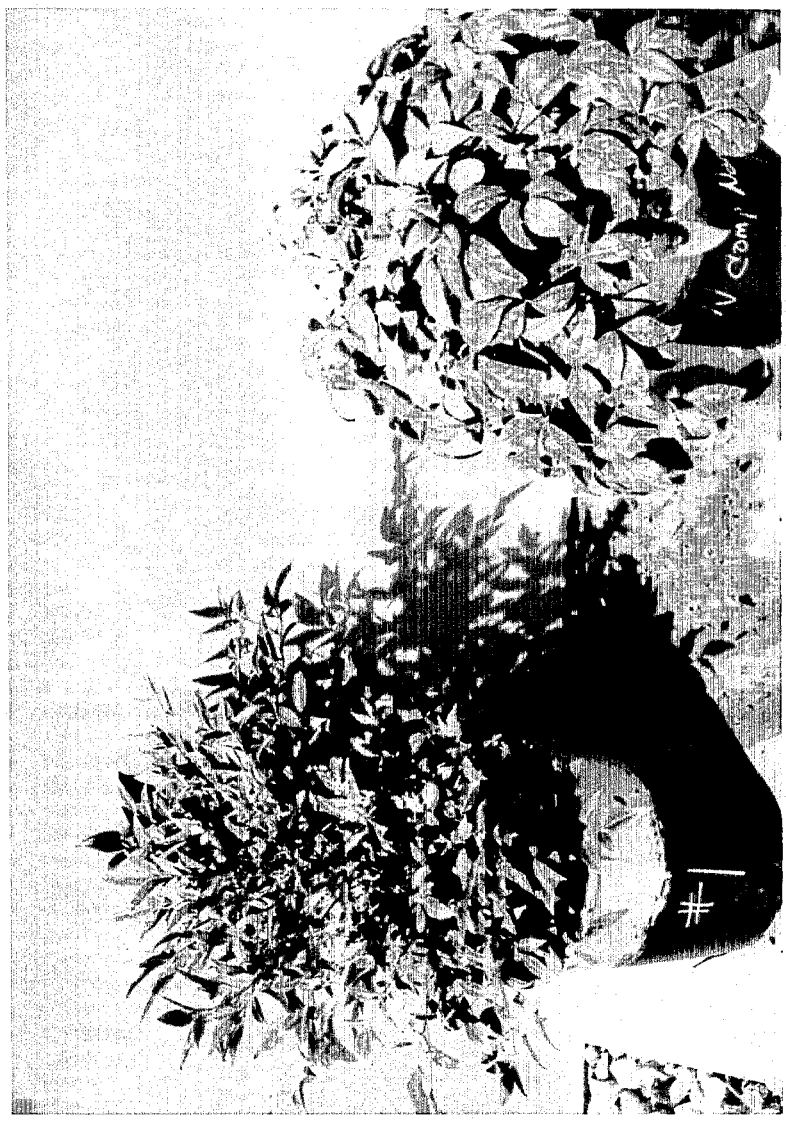
FIG. 2 is a side-by-side comparison of the new variety, shown on the left, with the parent variety, both plants growing in 1-gallon containers at an age of 18 months from cuttings.
Figure 3:
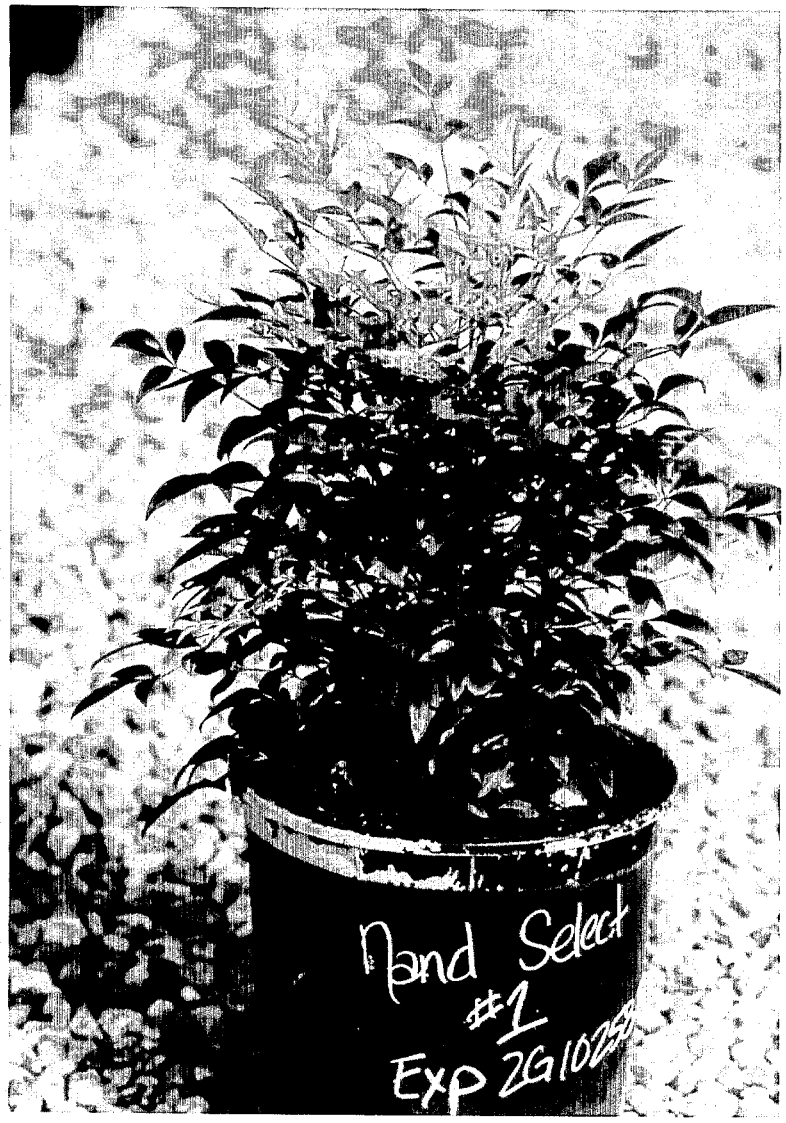
FIG. 3 is a photograph showing the winter coloration of the new variety. This is the same plant as in FIG. 1 but in a 2-gallon container and at an age of about 16 months.

Name: *Nandina domestica,* 'Gulf Stream' — Dwarf Heavenly Bamboo.

Family: Berberidaceae.

Parentage: A mutation originating in asexual produced population of *Nandina domestica* 'Compacta'.

Size: Ultimate height is unknown, as no specimen has reached full maturity. Present indications are that the full height will not exceed 75 centimeters and maybe less.

Growth habit: Dwarf, symmetrical densely compact, solitary form. Branches freely from basal and lateral buds, giving a full round erect shape.

Foliage: Alternate, tripinnately compound, evergreen. The leaflets are elliptic-lanceolate, slightly concave, ascending. Leaflet length varies between 13 mm and 51 mm, with a width of 13 mm at the widest point, based on a 15 leaf sample. The leaf margins are entire, apex acute, and the surface is glabrous. Stem character is upright.

Texture: Medium.

Flowers: None have been observed; for the species they are perfect, borne in upright panicle.

Disease and insect resistance: No disease or insect problems have occurred requiring other than normal nursery spraying practices common to all Nandinas.

Climatic range: Has withstood temperatures ranging from 20° to 102° F. without any harmful effects. While this specific plant has not been exposed to temperatures lower than 20° F., it is derived from a plant species which is hardy in Zone 6 USDA, where low temperatures range from 0° to 10° F.

Color: Mature leaf color, in The Royal Horticultural Society Colour Chart is under Fan 3 No. 139, Green Group No. A.

Emerging foliage is under: Fan 3 No. 153, Yellow—Green Group between No. A and B.Fan 4 No. 176, Greyed—Orange Group between No. B and C. Fan 3 No. 144, Yellow—Green Group between No. B and C. Fall coloration ranges in varying degrees from orange through red. Colorations are more intense with cold temperature.

Characteristics: *Nandina domestica* 'Gulf Stream' differs from its parent cultivar *Nandina domestica* 'Compacta' in its unique ascending growth habit which gives the plant an upward-reaching appearance. The branchlets and foliage are much more dense and compact than the 'Compacta' cultivar which has a more open, descending, willowy appearance. The new variety is dwarf and compact and branches freely from basal and lateral buds giving a full round, erect shape.

What is claimed is:

1. A new and distinct plant variety of *Nandina domestica* as shown and described, which is principally characterized by its symmetrical, densely compact, solitary form; free basal and lateral branching; greater foliage density; unique coloration of emerging foliage; and a mature height smaller than the common species and similar to the variety 'Compacta'.

* * * * *